United States Patent
Hsu

(10) Patent No.: US 6,662,646 B2
(45) Date of Patent: Dec. 16, 2003

(54) TEST TUMBLER IN A COLOR TEST MACHINE

(76) Inventor: Min-Chung Hsu, Lot D, Kuandu Apt. 8F, No. 10, Lane 33, Minzu Road Zhuwei, Danshui Chen, Taipei Hsien (TW)

( * ) Notice: Subject to any disclaimer, the term of this patent is extended or adjusted under 35 U.S.C. 154(b) by 251 days.

(21) Appl. No.: 09/897,980

(22) Filed: Jul. 5, 2001

(65) Prior Publication Data

US 2002/0178844 A1 Dec. 5, 2002

(30) Foreign Application Priority Data

Jun. 5, 2001 (TW) .................................. 90209311 U

(51) Int. Cl.⁷ ............................................. G01N 33/36
(52) U.S. Cl. ...................................................... 73/159
(58) Field of Search ........................ 73/159, 160, 866; 8/400

(56) References Cited

U.S. PATENT DOCUMENTS 5,374,006 A * 12/1994 Mheidle

FOREIGN PATENT DOCUMENTS

JP 0005957 * 1/1984 .................. 73/159

* cited by examiner

Primary Examiner—Robert Raevis
(74) Attorney, Agent, or Firm—Troxell Law Office PLLC

(57) ABSTRACT

A test tumbler in a color test machine has an outer cylinder, a cloth wound device, at least a knock rod, and an upper cap. The outer cylinder has a hollow chamber, and an open end and a closed end. The cloth wound device has a piercing circumference, and a sample cloth is wound on the outer surface or on the inner surface. At least a knock rod is received in the cloth wound device. The upper cap is detachably blocking the open end of the outer cylinder. Once the cloth wound device with the wound cloth and the knock rod is placed in the outer cylinder together with a dyestuff, the test tumbler is put in a receiving recess of the color test machine after the upper cap blocking the open end of the outer cylinder. The test tumbler can be rotated as soon as the color test machine starts to run such that the knock rod can strike the cloth wound device to perform a dyeing operation on the wound cloth evenly.

6 Claims, 5 Drawing Sheets

TEST TUMBLER IN A COLOR TEST MACHINE

BACKGROUND OF THE INVENTION

1. Field of the Invention

The present invention relates to a test tumbler in a color test machine, and, more particularly, to an improved test tumbler, with which a sample cloth can dyed evenly and the color dyed can be fixed integrally easily and effectively.

2. Description of Related Art

Usually, a test color for a sample cloth or yarn is performed by way of a test tumbler receiving small amount of the sample cloth or yarn together with the dyestuff and rotating with the color test machine for a period of time. In this way, the dyestuff can seep into the fiber structure of the sample cloth. Hence, the test tumbler forms an enclosed space to execute a reaction of dye in case of the sample cloth being placed in the test tumbler.

The conventional test tumbler is a pure tumbler with a cap and, mostly, it provides a simple configuration. In practice, the sample cloth is wound before being placed in the test tumbler and then, a preset color and quantity of the dyestuff before the test tumbler being covered with the cap and being put in a warming up recess. Of course, a simple frame also used for winding the sample cloth. Anyhow, the test tumbler in the recess of the color test machine is subjected to a pure rotation so that it results in the sample cloth being dyed unevenly to affect the quality tremendously.

On the other hand, it is often necessary to conduct a treatment of color fixing after dyeing, that is, the reaction of dyeing can be stopped and the dyed color can be adhered to the sample cloth reliably after being treated with color fixing. In order to perform the treatment of color fixing, the conventional operation way is to open the upper cap and pour the color fixer into the test tumbler. Then, the test tumbler is rotated again to carry out the operation of color fixing. However, the temperature is maintained over 60° C. (normally is 135° C.) during performing the dyeing job and it is dangerous to conduct the treatment of color fixing under such high temperature.

SUMMARY OF THE INVENTION

An object of the present invention is to provide a test tumbler in a color test machine, which has a cloth wound device and at least a knock rod to perform the dyeing job for the sample cloth evenly.

Another object of the present invention is to provide a test tumbler in a color test machine, which further offers a color fixer supply device to be attached to the test tumbler so as to perform the treatment of color fixing easily and reliably.

BRIEF DESCRIPTION OF THE DRAWINGS

The present invention can be more fully understood by referencing to the following description and accompanying drawings, in which.

DETAILED DESCRIPTION OF THE PREFERRED EMBODIMENTS

Figure 1:
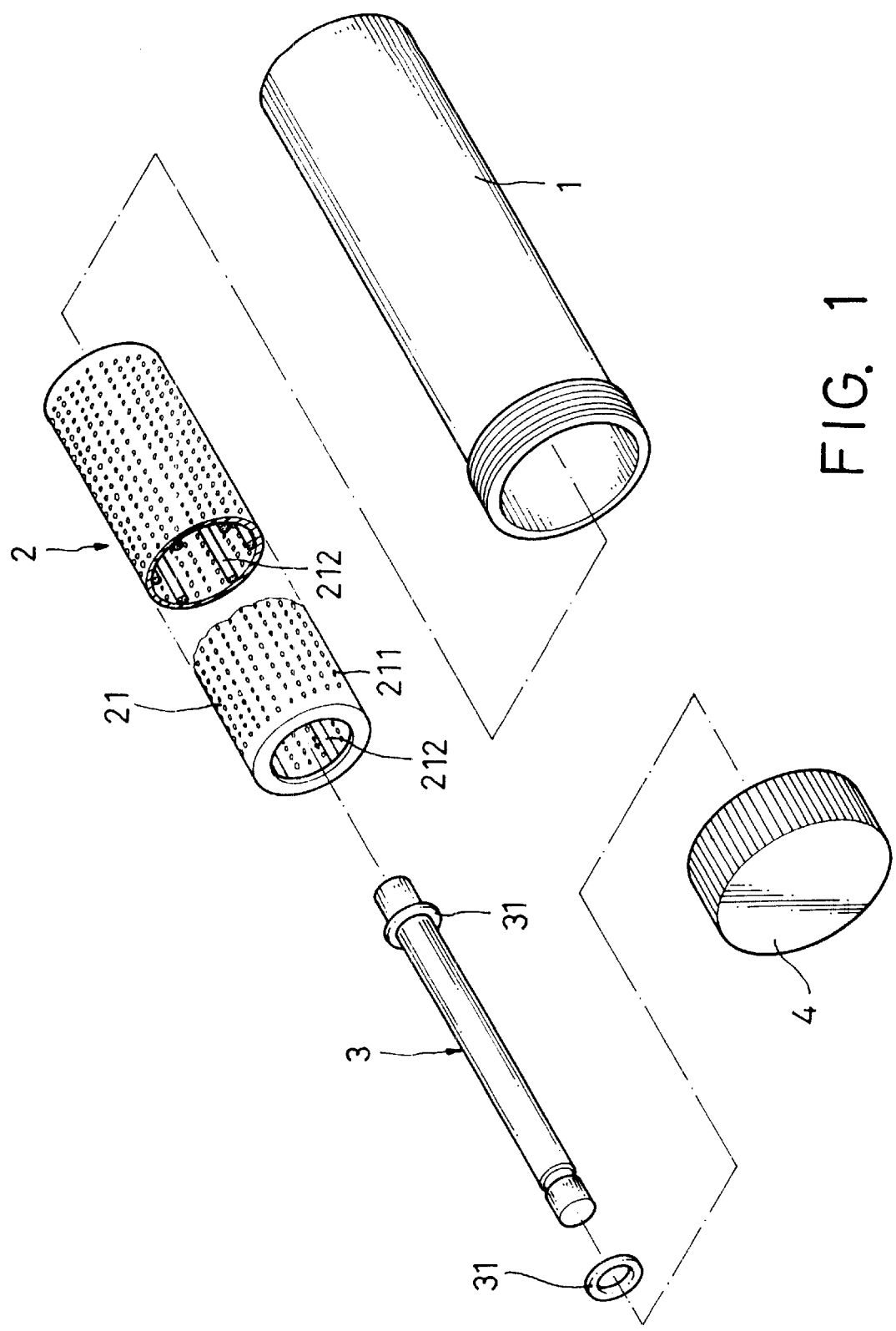
FIG. 1 is an exploded perspective view of a test tumbler in a color test machine according to the present invention illustrating a cloth wound device thereof being a filter cylinder.

Referring to FIGS. 1 to 6, a test tumbler in a color test machine according to the present invention basically comprises an outer cylinder 1, a cloth wound device 2, at least a knock rod 3, an upper cap 4, or a color fixer supply device 5.

The outer cylinder 1 is an elongated cylinder with a closed end to constitute an inner chamber for receiving the cloth wound device 2, the knock rod 3, and a sample cloth to be dyed. The outer cylinder 1 at the open end thereof can engage with the upper lid 4 and with the color fixer supply device 5. The size of the outer cylinder 1 is corresponding to a receiving recess such that the test tumbler can be kept in the receiving recess.

Figure 2:
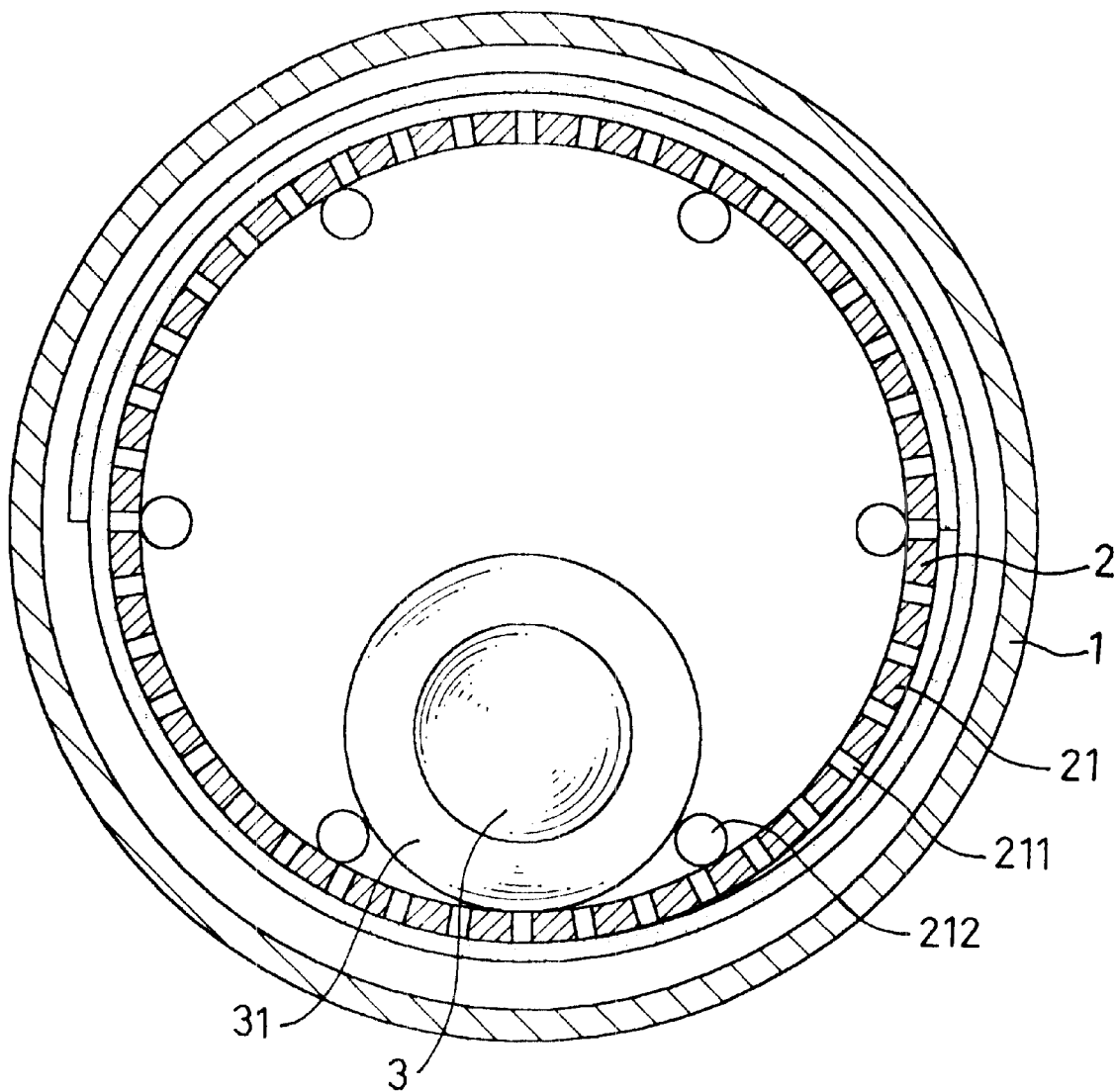
FIG. 2 is sectional view of the test tumbler shown in FIG. 1 after assembling.

The cloth wound device 2 is for winding a sample cloth and it is a filter cylinder 21 shown in FIGS. 1 and 2. The cylinder wall of the filter cylinder 21 is provided with a plurality of filter apertures 211 for being passed through by the dyestuff. In order to provide an effect of knock, the inner wall surface of the filter cylinder 21 is attached with a plurality of sticks 212, and it is preferable that the sticks 212 are equally spaced apart from each other along the axial direction of the filter cylinder 21 and each stick 212 has an identical size respectively. The outer diameter of the filter cylinder 21 is less than the inner diameter of the outer cylinder 1 such that a clearance between the outer cylinder 1 and the filter cylinder 21 is greater than the thickness of the wound sample cloth.

The knock rod 3 is elongated shape with both end parts thereof being attached with at least an annular flange 31 respectively in case of the filter cylinder 21 being used. It is preferable that the annular flange 31 is made of elastic material. The knock rod 3 may be solid, hollow, or hollow with a plurality of apertures for being passed through by the liquid dyestuff.

The upper cap 4 has a size corresponding to the outer cylinder 1 so that the upper cap 4 can engage with the outer cylinder 1 by way of fastening device such as screw threads.

Referring to FIGS. 1 to 2 again, the sample cloth is wound to surround the filter cylinder 21 and the knock rod 3 is placed in the filter cylinder 21 while the test tumbler of the present invention is in use. Then, the filter cylinder 21 is inserted into the outer cylinder 1 and the dyestuff is added in the outer cylinder 1 too before the upper cap 4 being attached to the outer cylinder 1. Finally, the enclosed outer cylinder 1 is located at the receiving recess in the color test machine. When the color is to be tested, the tumbler in the recess may rotate synchronously as soon as the color test machine starts to run. The knock rod 3 may stay at the lower part of the tumbler because of the gravity and may jump upward at the time of striking the sticks during the rotating process such that the sample cloth is knocked indirectly. Due to the equal rotational speed, the sample cloth can be tinted evenly.

Figure 3:
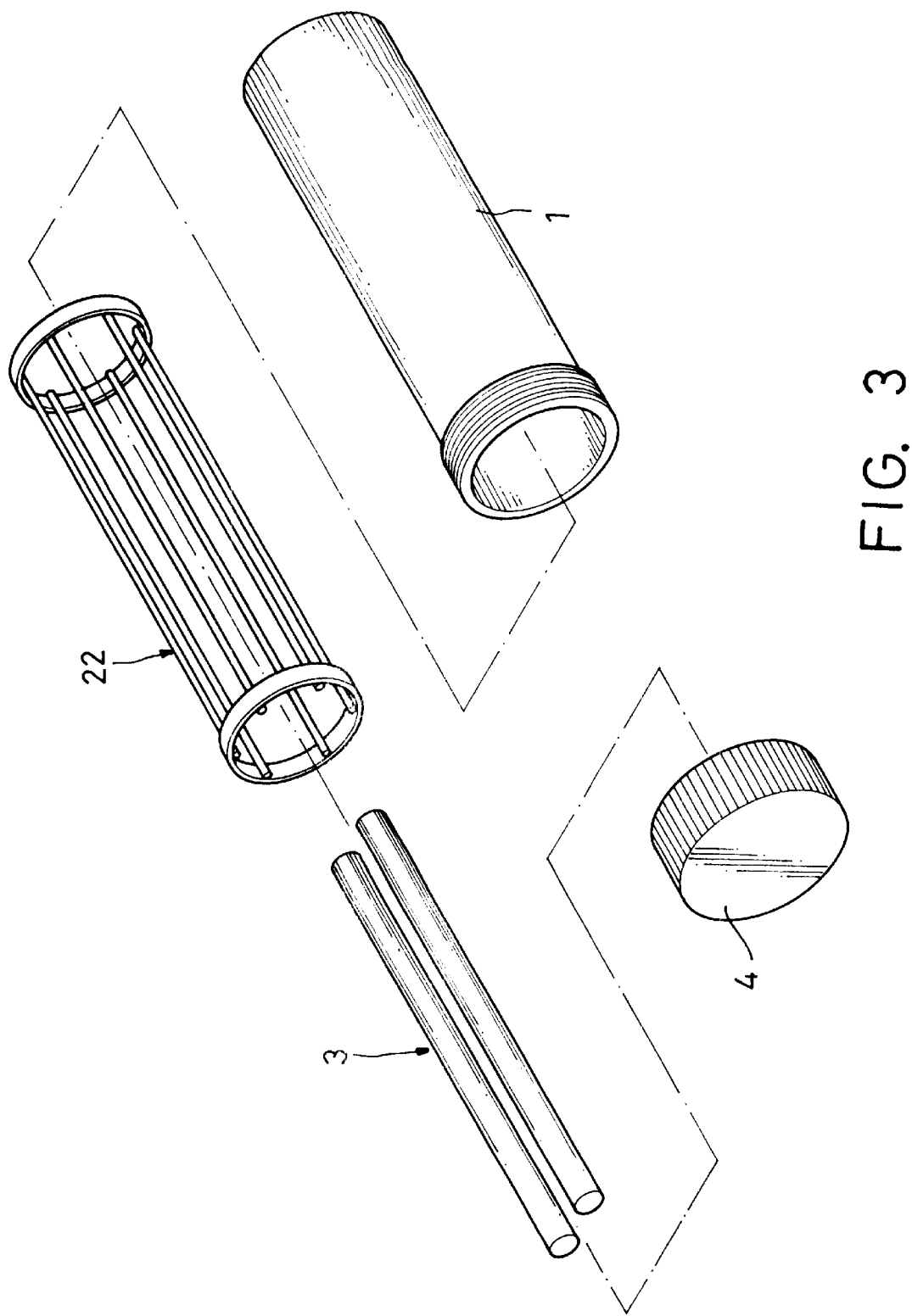
FIG. 3 is an exploded perspective view of a test tumbler in a color test machine according to the present invention illustrating a cloth wound device thereof being a filter grate.

Referring to FIG. 3, another embodiment for the cloth wound device 2 and the knock rod is illustrated. A cylindrical filter grate 22 is used instead of the filter cylinder 21, and the filter grate 22 comprises a plurality of longitudinal bars. The knock rod is a plain elongated rod and the sample cloth is wound around at least a knock rod 3 before the wound sample cloth is placed in the filter grate 22 while in use. Then, the filter grate 22 and knock rod 3 with the wound sample cloth are inserted into the outer cylinder 1 and the dyestuff is added in the outer cylinder 1 before the upper cap 4 being attached to the outer cylinder 1. Finally, the assembled tumbler of the present invention is put in the receiving recess of the color test machine such that the subsequent dyeing job for the sample cloth can be performed afterward. As soon as the dyeing job is processed, the knock rod 3 rolls over and over along the rotating filter grate 22 to knock the sample cloth. Hence, a better effect of dyeing can be obtained.

As it has been mentioned above, the color fixer supply device 5 can be used instead of the upper cap 1 in order to treat the operation of fixing color integrally. Next, referring to FIGS. 4, 5, and 6 again, the color fixer supply device 5 comprises a cup 51, a back-up ring 52, an inner magnet piece 53, an outer magnet piece 54, and a ball 55.

Wherein, the cup 51 is cylindrical and made of non-magnetized material with an open end. The cup 51 at the inner wall thereof has an annular step 511 for locating the back-up ring 52. In practice, the cup 51 is used for containing the color fixer.

The back-up ring 52 can locate the inner magnet piece 53 after being located at the annular step 511.

The inner magnet piece 53 is a magnetic substance to absorb the outer magnet piece 54 and a sealing ring 531 surrounds the inner magnet piece 53 to prevent from leakage.

The outer magnet piece 54 is a magnetic substance too so that the outer magnet piece 54 and the inner magnet piece 53 can absorb each other mutually. The ball 55 is made of non-magnetized material such as stainless steel so that the ball 55 cannot be absorbed by the outer magnet piece 54. It is preferable that the bail 55 is round.

Figure 4:
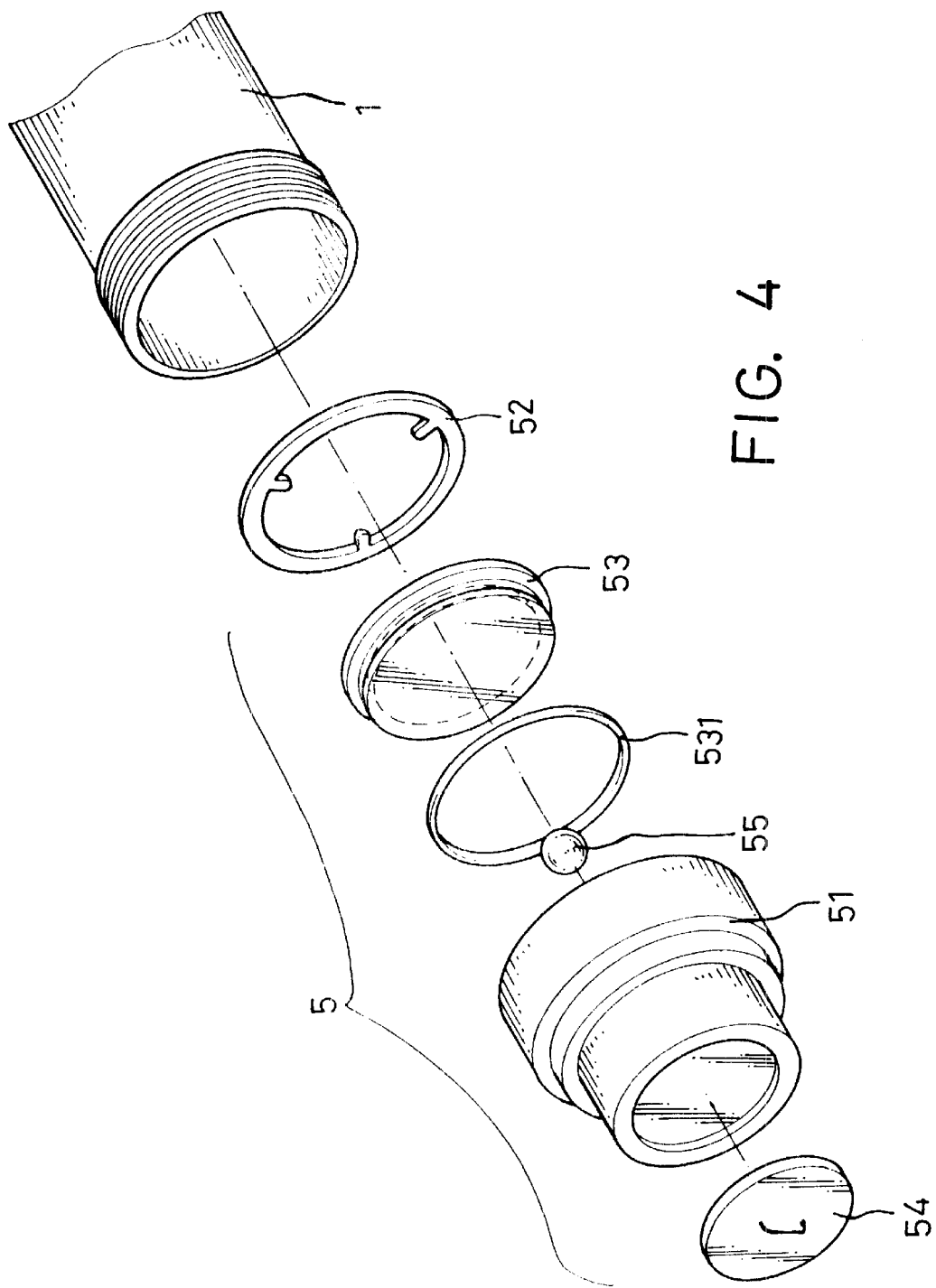
FIG. 4 is an exploded perspective view of a color fixer supply device used in the test tumbler of the present invention.
Figure 5:
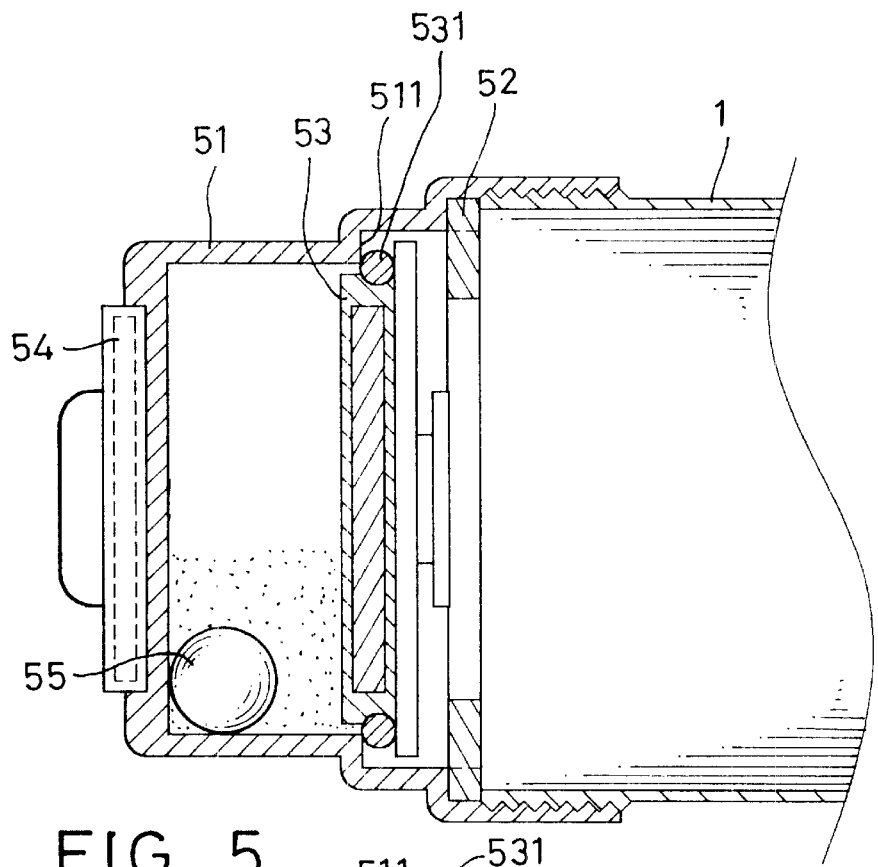
FIG. 5 is a sectional view of the color fixer supply device shown in FIG. 4 after assembling.
Figure 6:
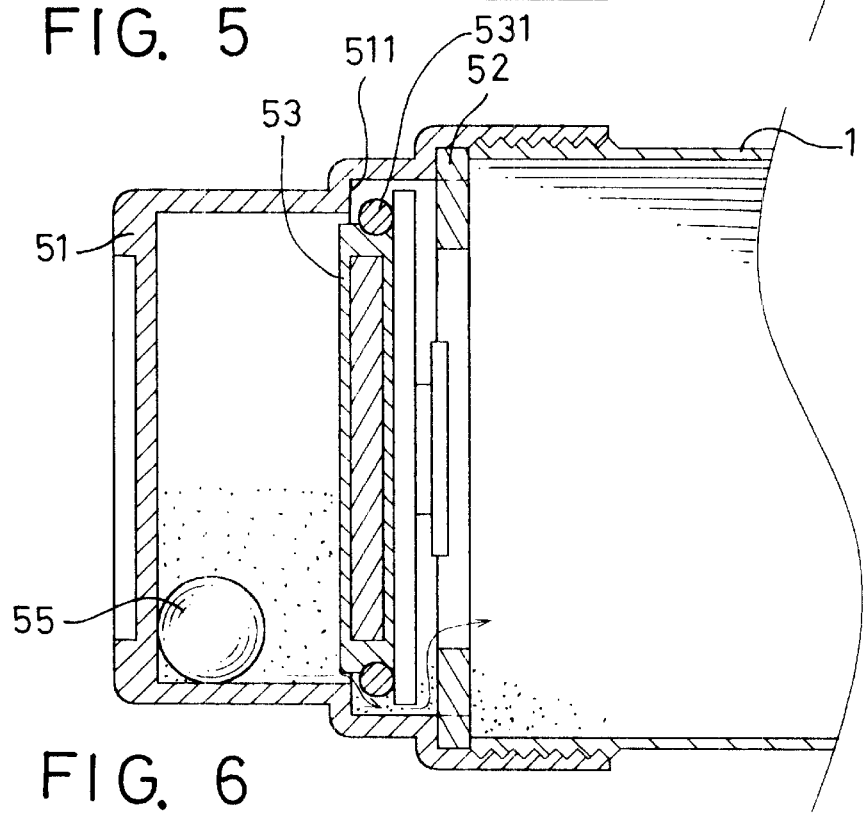
FIG. 6 is a sectional view similar to FIG. 5 illustrating the color fixer supply device in a state of being actuated.

Referring to FIGS. 4 to 6 further, while the cooler fixer supply device 5 is in use, the cooler fixer and the bail 55 are received in the cup 51 and the back-up ring 52 is placed on the annular step 511. The inner magnet piece 53 with the sealing ring 531 is placed on the back-up ring 52 and the cup 51 is engaged to the outer cylinder 1. The upper cap 4 is added and absorbed by the outer magnet piece 54. In the mean time, the inner magnet piece 53 and the outer magnet piece 54 attract each other so as to join together and the sealing ring 531 blocks the periphery of the cup 51 such that the color fixer may not seep into the test tumbler. The ball 55 rolls in the cup 51 to agitate the color fixer.

As soon as the dyeing job is complete and the color fixing job is to be performed, the outer magnet piece 54 is moved away the upper cap 4 and the inner magnet piece 53 losses the attraction force thereof such that a clearance is formed between the sealing ring 531 and the cup 51 in addition to the impact of the ball 55. In this way, the color fixer may seep into the test tumbler through the clearance during executing the job of color fixing, and it is slow for the color fixer to be fed so that the color fixing on the sample cloth can be performed evenly to promote the quality of color fixing thereof.

It is appreciated from the preceding detail description that the test tumbler of the present invention can intensify the homogeneousness of color fixing in addition to a better effect of dyeing being obtained. These advantages are not possible for the conventional test tumbler in a color test machine to reach effectively.

While the invention has been described with reference to preferred embodiments thereof, it is to be understood that modifications or variations may be easily made without departing from the spirit of this invention, which is defined in the appended claims.

What is claimed is:

1. A test tumbler in a color test machine, comprising:
   an outer cylinder with an closed end, having a hollow chamber, and an open end opposite to the closed end;
   a cloth wound device with an outer surface and an inner surface, having a piercing circumference, and winding a sample cloth on the outer surface or on the inner surface;
   at least a knock rod, being received in the cloth wound device; and
   an upper cap, detachably blocking the open end of the outer cylinder;
   whereby, once the cloth wound device with the wound cloth and the knock rod is placed in the outer cylinder together with a dyestuff, the whole test tumbler is put in a locating recess of the color test machine after the upper cap blocking the open end of the outer cylinder; and the test tumbler can rotate as soon as the color test machine states to run such that the knock rod can strike the cloth wound device to perform a dyeing operation on the wound cloth evenly.

2. The test tumbler in a color test machine according to claim 1, wherein the cloth wound device is a filter cylinder with a plurality of filtering apertures on a circumferential wall thereof; an inner wall surface being attached with a plurality of sticks along an axial direction of the filter cylinder; the knock rod is attached with at least two annular projection rings; and the sample cloth is wound surrounding the filter cylinder.

3. The test tumbler in a color test machine according to claim 1, wherein the cloth wound device is a filter grate comprising a plurality of bars and the sample cloth is wound on the knock rod before being placed in the filter grate.

4. The test tumbler in a color test machine according to claim 1, wherein the knock rod is solid, hollow, or hollow with apertures on a circumferential wall thereof.

5. The test tumbler in a color test machine according to claim 1, wherein the upper cap is a color fixer supply device, and the color fixer supply device comprises a non-magnetized cup with an open end, a back-up ring, an inner magnetic piece with a sealing ring, and an outer magnetic piece; the cup has an annular step on an inner wall surface thereof for locating the back-up ring; as soon as the color fixer is poured in the cup and engages with the outer cylinder, the outer magnetic piece is attracted by the inner magnetic piece and the sealing ring seals the cup tightly; and once the outer magnetic piece is removed, a clearance is formed between the sealing ring and the cup to admit the color fixer little by little such that the color fixer can seep into the outer cylinder slowly to perform a function of color fixing.

6. The test tumbler in a color test machine according to claim 5, wherein a ball is added in the cup to agitate the color fixer.

* * * * *